(12) United States Patent
Mellbin

(10) Patent No.: US 9,878,060 B2
(45) Date of Patent: Jan. 30, 2018

(54) STERILIZATION DEVICE AND AN ELECTRON BEAM EMITTER

(71) Applicant: TETRA LAVAL HOLDINGS & FINANCE S.A., Pully (CH)

(72) Inventor: Håkan Mellbin, Hörby (SE)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 0 days.

(21) Appl. No.: 15/120,079

(22) PCT Filed: Jan. 21, 2015

(86) PCT No.: PCT/EP2015/051070
§ 371 (c)(1),
(2) Date: Aug. 18, 2016

(87) PCT Pub. No.: WO2015/124356
PCT Pub. Date: Aug. 27, 2015

(65) Prior Publication Data
US 2017/0056539 A1    Mar. 2, 2017

(30) Foreign Application Priority Data

Feb. 19, 2014 (SE) ...................................... 1450200

(51) Int. Cl.
*A61L 2/00* (2006.01)
*A61L 2/08* (2006.01)
(Continued)

(52) U.S. Cl.
CPC .............. *A61L 2/087* (2013.01); *B65B 55/08* (2013.01); *G21K 5/02* (2013.01); *H01J 37/07* (2013.01);
(Continued)

(58) Field of Classification Search
CPC .. A61L 2/087; A61L 2202/11; A61L 2202/23; B65B 55/08; H01J 37/242; H01J 37/07; G21K 5/02
(Continued)

(56) References Cited

U.S. PATENT DOCUMENTS 3,486,064 A    12/1969  Stauffer
4,058,697 A    11/1977  Sokolov et al.
(Continued)

FOREIGN PATENT DOCUMENTS

| EP | 2 419 909 B1 | 2/2012 |
|---|---|---|
| WO | WO 2010/118982 A1 | 10/2010 |
| WO | WO 2014/095838 A1 | 6/2014 |

OTHER PUBLICATIONS

International Search Report (PCT/ISA/210) dated May 4, 2015, by the European Patent Office as the International Searching Authority for International Application No. PCT/EP2015/051070.
(Continued)

*Primary Examiner* — Michael Maskell
(74) *Attorney, Agent, or Firm* — Buchanan Ingersoll & Rooney PC

(57) ABSTRACT

Sterilization device, in particular for sterilization of packaging material, comprising a first chamber, a barrier element and a connection area. The first chamber is adapted to provide charge carriers for sterilization, and the connection area is connected to a third chamber so that the barrier element forms at least one part of the boundary of a volume in which a first atmosphere exists.

16 Claims, 9 Drawing Sheets

Figure 1:
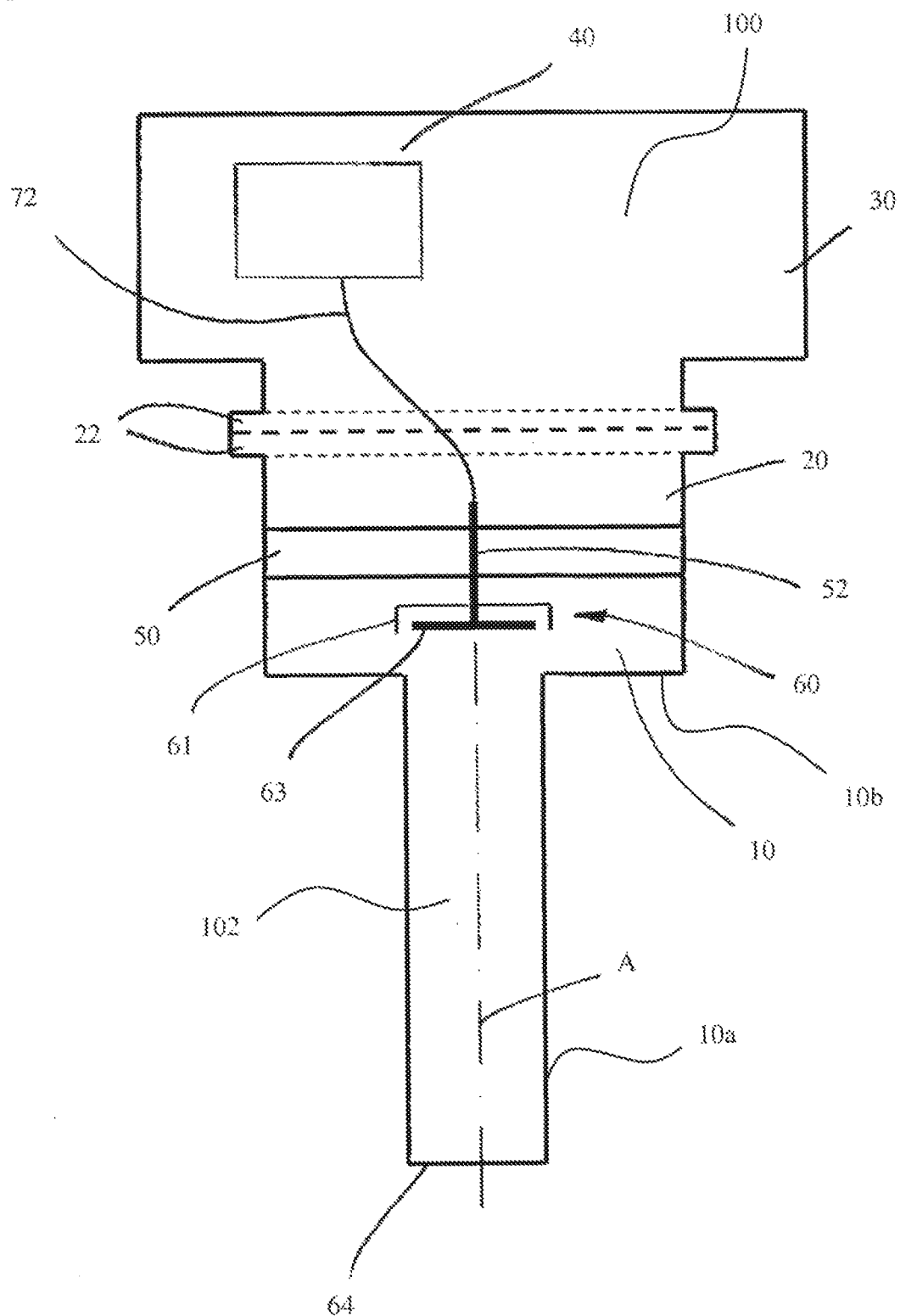

(51) Int. Cl.
    *B65B 55/08*     (2006.01)
    *G21K 5/02*     (2006.01)
    *H01J 37/07*     (2006.01)
    *H01J 37/24*     (2006.01)

(52) U.S. Cl.
    CPC ......... *H01J 37/242* (2013.01); *A61L 2202/11* (2013.01); *A61L 2202/23* (2013.01)

(58) Field of Classification Search
    USPC .................................. 250/453.11–455.11
    See application file for complete search history.

(56) References Cited

U.S. PATENT DOCUMENTS

| | | | |
|---|---|---|---|
| 2008/0007378 A1* | 1/2008 | Hanser | H01F 41/08 336/5 |
| 2012/0025106 A1* | 2/2012 | Apel | G21K 5/04 250/492.3 |
| 2015/0336701 A1* | 11/2015 | Eidebakken | A61L 2/087 53/426 |

OTHER PUBLICATIONS

Written Opinion (PCT/ISA/237) dated May 4, 2015, by the European Patent Office as the International Searching Authority for International Application No. PCT/EP2015/051070.

Swedish Office Action dated Oct. 7, 2014 by the Swedish Patent Office in Swedish Application No. 1450200-9 (5 pages).

\* cited by examiner

STERILIZATION DEVICE AND AN ELECTRON BEAM EMITTER

This invention relates to a sterilization device, in particular for sterilization of packaging material and an electron beam emitter, in particular for sterilization of packaging material.

Sterilization devices or electron beam emitters, respectively, are basically known from the prior art. In e. g. liquid food packaging, electron beam irradiation has been considered as a promising alternative for sterilizing purposes, for which wet chemistry involving hydrogen peroxide has been the traditional technical platform. Sterilization devices or electron beam emitters, respectively, provide sterilization of the packaging material thus eliminating the negative consequences of wet chemistry within the packaging machine. However, sterilization devices or electron beam emitters, respectively, known from the prior art are in general heavy, too big and uncomfortably to use. E. g. EP 2 419 909 B1 discloses a rather compact sterilization device, however— amongst others—the problem exists that the power supply and the electron beam emitter are located within a common housing which makes maintenance very difficult or even not possible. Another challenge is to provide a sufficient protection from radiation for the electric components that are located within the sterilization device.

Therefore, it is an object of the current invention to provide a sterilization device, in particular for sterilization of packaging material and an electron beam emitter, in particular for sterilization of packaging material, to maintain high flexibility, cost effectiveness and a suitable protection for the installed electronic components. This object is achieved by a sterilization device according to claim 1 and by an electron beam emitter according to claim 15. Additional advantages and features of embodiments of the current invention are defined in the dependant claims.

According to the invention a sterilization device, in particular for sterilization of packaging material, comprises a housing and a barrier element, wherein the housing comprises at least a first chamber, wherein the first chamber is adapted to provide charge carriers for sterilization, characterized in that the housing is connected to a third chamber so that the barrier element forms at least one part of the boundary of a volume in which a first atmosphere exists. According to one or more embodiments the first chamber comprises means for generating charge carriers, in particular for packaging containers. The charge carriers are high voltage electrons that form a high voltage electron beam or beams, respectively. Such packaging containers can be used for liquid, semi-liquid and/or solid medium. They can for example be used in the food industry or in the medical or biological area (to transport and protect biological and medical substances). However, the sterilization device may also be used for sterilization of devices, such as medical or biological devices, or food etc. One main object of the third chamber is to provide the electric power for the electron generator in the first chamber. In other words, the third chamber preferably comprises means for providing the electric power, such as a high voltage power supply unit. The barrier element limits or defines the first chamber within said housing. In particular, the barrier element protects a second atmosphere in the first chamber. On the other hand, the barrier element forms at least a part of the boundary of the volume in which the first atmosphere exists. This means, that different atmospheres can be provided within the first chamber and within the volume. The barrier element is gas tight.

As a consequence, the atmosphere in the first chamber can be adapted for the generation of electrons and the atmosphere in the volume, that comprises the means for generating the electric power (for the first chamber), can be ideally adapted to the appropriate requirements. As a consequence, ideal conditions for e. g. electric components inside the volume can be provided. Advantageously, the barrier element forms at least one part of the boundary of the volume. The barrier element is then placed in between the first and second atmosphere.

To realize the connection between the housing and the third chamber, the housing comprises an appropriate connection area. Similarly, the third chamber preferably also comprises an appropriate connection area that fits to the connection area of the housing. According to one or more embodiments the connection areas are adapted to provide a form and/or a force fit connection between each other. In other words, the third chamber comprises a connection area or areas that fit to the connection area of the housing. According to one or more embodiments the connection areas are formed as flanges. For the connection itself, there can be used connection elements, such as bolts or screws (first connection elements). This means, that the connection areas or the flanges, respectively, comprise appropriate holes (second connection elements) so that the first connection elements can be arranged. Alternatively or in addition, at least one first connection element can be already integrated in the connection area or in the flange, respectively. This makes it very easy to attach the connection areas to each other or to demount the sterilization device, in particular to remove the third chamber from the other parts.

Cross sections of the connection areas can have different geometries. According to one or more embodiments the connection areas are basically round, in particular basically circular. However, also oval, rectangular, quadratic or polygonal cross sections are possible. Advantageously, the connection areas can comprise a sealing, such as an o-ring or a sealing mass to protect and keep the first atmosphere inside the housing. In the first atmosphere, there can exist a specific temperature or a specific pressure. In particular, the volume can be filled with a specific medium which characterizes the first atmosphere. Expediently, the atmosphere is ideally adapted to the appropriate requirements. In particular, the atmosphere is adapted to insulate the components that generate and transforms the electric power inside the volume and it is further adapted to insulate the transportation of the electric power to the housing or the first chamber, respectively. Advantageously, the housing and the third chamber do not have a common housing. Instead, they can be advantageously demounted as they are connected via the connection areas. As a consequence, the possibility of simple maintenance can be improved.

According to one or more embodiments the volume is formed by the third chamber or by the third chamber and a second chamber. In other words, the volume is the volume inside the third chamber or the volume inside the third chamber and a second chamber, wherein the barrier element forms at least one part of the boundary of the volume. According to one or more embodiments a second chamber is formed between the first and the third chamber. This may be realized by an offset between the barrier element and an end of the housing. The second chamber is a part or an element of the housing, wherein the second chamber or the first chamber can comprise the connection area. Preferably, the first and the second chamber are formed by the housing, wherein the housing comprises the connection area that is formed as a flange according to one or more embodiments.

If the second chamber is provided, advantageously, the atmosphere in the second and in the third chamber is the same. In other words, the volume is at least partly formed by the second and the third chamber. In a preferred embodiment, a power supply unit that is adapted to provide the electric power for the sterilization means in the first chamber is located within the third chamber. It goes without saying that the volume or the third chamber, respectively, can comprise a plurality of power supply units or—in general—electric components.

Expediently, the first chamber comprises an electron generator, wherein the electron generator comprises a cathode housing and a filament. In other words, the housing that comprises the first chamber is an electron beam emitter. In the following a preferred embodiment is described. The filament is adapted to emit the electrons and to thereby form an electron beam or electron beams. In use, the electron beam is generated by heating the filament. When an electrical current is fed through the filament, the electrical resistance of the filament causes the filament to be heated to a temperature in the order of 2000° C. This heating causes the filament to emit electrons. The electrons are accelerated towards an electron exit window by means of a high-voltage potential between the cathode housing and the electron exit window. Subsequently, the electrons pass through the electron exit window and continue towards a target area, for example the material or area, respectively, that has to be sterilized. The first chamber comprises a second atmosphere, preferably a vacuum. The first chamber may be either hermetically sealed or connected to a pump for maintenance of the vacuum. According to one or more embodiments, the housing comprising electron generator is an electron beam emitter for sterilizing the interior of (e. g. ready-to-fill) packaging containers. The electron beam emitter comprises the electron generator that is enclosed in the vacuum chamber which is the first chamber. The vacuum chamber is provided with the electron exit window. Expediently, the vacuum chamber is made up of two cylindrical bodies with substantially circular cross sections. The cylindrical bodies have a common longitudinal axis. The first cylindrical body has an end surface, in a plane being perpendicular to the axis, being provided with the electron exit window. The electron exit window is circular and extends over most of the end surface. The window can be made of a metallic foil, such as for example titanium, and can have a thickness in the order of about 4-12 µm. A supporting structure provided with holes supports the foil from inside the vacuum chamber. The supporting structure is for example made of aluminum or copper. A diameter of the first body is small enough to be inserted e. g. into the ready-to-fill packaging container. The cross section of the first body is dimensioned such that it can be guided through an opening of the packaging container. The second body is provided with the electron beam generator, and the diameter of the second body is larger that the first body.

In one or more embodiments the packaging material is basically tube-shaped, and the sterilization device or the electron beam emitter is adapted for sterilization of at least the interior surface of the tube-shaped packaging material through an opening of the tube-shaped packaging material. The tube-shaped packaging material is a packaging container. The term "tube shaped" comprises no limitations concerning the possible form of the cross-section. This means that the cross section can be round, rectangular, circular, polygonal and/or angular and especially, the cross section of the basically tube shaped packaging material does not have to be constant along the axis. Without limiting the generality the basically tube-shaped packaging material is sometimes named "packaging container" in the following.

The opening of the packaging container is adapted to enable an insertion of the emitter. The packaging container is closed at its other end portion opposite the opening, and it extends along an axis.

The packaging container can for example be made of a plastic material such as for instance PET, or be made of a (laminated) carton material. With regard to the later a common type of laminated carton material is the ones comprising a core layer of paper or paperboard and one or more barrier layers of, for example, polymer material or aluminium foil. An increasingly common packaging type is the "carton bottle" manufactured in a filling machine in that packaging blanks of the above-described packaging laminate are formed and sealed as a sleeve. Said sleeve is closed in one end in that a top of thermoplastic material is injection moulded directly on the sleeve end portion. The sheets of packaging laminate may be cut from a magazine reel of packaging laminate.

Advantageously, the opening of the packaging container, e.g. the spout or a bottom of the packaging container, has to be big enough so that at least the portion of the electron beam emitter comprising the electron exit window can be passed through it, to sterilize in particular the interior surface of the packaging container. In one or more embodiments the emitter has a round, in particular a circular cross section that is basically constant. A diameter of the cross-section lies within a range of about 5-100 mm.

In another preferred embodiment, the electron beam emitter is adapted for exterior sterilization of packaging containers. Such packaging containers may also be used for web sterilization, for sterilization of medical or biological devices or for food etc. Such an electron beam emitter comprises an elongate tubular body. A longitudinal axis of the elongate tubular body is basically parallel to a plane of an electron exit window, and hence thereby perpendicular to a main direction of the electron beam as it exits the window. The electron exit window provides an outlet for the electrons from a vacuum chamber inside the tubular body. The electron exit window is substantially rectangular having its longest extension in a direction parallel to the longitudinal axis of the electron beam emitter. The electron exit window is substantially flat and protrudes from the perimeter surface of the tubular body. The electron exit window can be made of a metallic foil, such as for example titanium, and can have a thickness in the order of about 4-12 µm. A supporting structure provided with holes supports the foil from inside the vacuum chamber. The supporting structure is for example made of aluminum or copper.

Exterior sterilization of packaging containers means sterilization of the exterior surfaces of the packaging containers. For example, exterior sterilization may be accomplished by arranging two electron beam emitters, of the above mentioned type, opposite each other, with their electron exit windows facing each other, forming a gap in between them. The electron beams generated by the second electron beam emitters overlap each other and form a unified electron cloud filling the gap. The gap may be the entry to an aseptic zone comprising a filling station, for filling content into the packaging container, and a sealing station, for sealing the opening of the packaging container. As such the unified cloud forms an irradiation barrier or sterilization sluice at least covering the entry region. The distance between the electron exit windows 40 is adapted to the size of the radial cross section of the packaging container, and should be kept only slightly larger such that the packaging container can easily be passed between them. An exemplary application in which the invention can be used is described in the international application No. PCT/EP2013/076870 filed by the applicant. Both exterior sterilization, as described above, and interior sterilization, as previously described, are carried out.

In one or more embodiments the volume comprises an insulation medium that is adapted to provide an insulation effect, wherein the insulation medium is preferably an insulation fluid or gas, such as nitrogen. In other word, the atmosphere of the volume provides the insulation effect. In other words, the first atmosphere is a insulation atmosphere. According to one or more embodiments, the second and the third chamber are advantageously filled with the insulation medium. The insulation medium is gas, in particular nitrogen. Nitrogen is a dielectric gas that has very good insulation qualities, as it has a high dielectric strength which enables to prevent or quench electric discharges. According to one or more embodiments the gas is pressurized. Preferably, a pressure of the insulation medium, in particular the gas, such as nitrogen, lies within a range of about 1.5 to 3.5 bar. In one or more embodiments the range is 2 to 3 bar, and in one or more embodiments the range is 2.5 to 3 bar. This improves the insulation effect. Expediently, the insulation medium protects both the power supply unit (and the other electric components in the volume) and an electric connection from the power supply unit to the first chamber inside the volume. According to one or more embodiments the second and/or the third chamber comprises at least one valve that is adapted to fill or drain the chambers with or from the insulation medium. By draining the insulation medium, the second and the third chamber can be easily separated and repaired/exchanged separately. It goes without saying that the above mentioned features concerning the insulation do not depend on the existence of the second chamber. It is sufficient to make sure that the atmosphere has contact with the barrier element.

Advantageously, the barrier element comprises at least one interface, in particular an electric interface. The interface is adapted to provide an electric connection between the volume and the first chamber. The barrier element is adapted to separate the first chamber from the volume, in particular it is adapted to separate the appropriate atmospheres. However, an electric connection has to be realized to supply the first chamber with e. g. electric power. The interface is adapted to provide the electric connection through the barrier element and the interface comprises according to one or more embodiments at least one connection element at each of its end portions. A connection element can be for example a connector or a bushing or a plurality of these components. The element that provides the electric connection through the barrier element can be e. g. a cable. However, this functionality can also be provided by the connection element or elements itself. The interface may also be a cable that is integrated into the barrier element and that has appropriate connectors or jacks at its end portions. The interface provides expediently an electric connection from the electron generator in the first chamber to the barrier element and from the barrier element to the power supply unit in the third chamber or in the volume, respectively. As the barrier element forms the boundary of the volume, the barrier element has contact with the atmosphere, in particular with the insulation atmosphere. As a consequence also the electric interface, in particular the connection element or elements that are directed to the side of the volume are also in contact with the insulation atmosphere. Thus, they are preferably also insulated. According to one or more embodiments, the barrier element comprises means for protection against radiation, such as x-rays. In particular, lead or layers of lead, respectively, can be inserted into the barrier element, wherein the layers preferably extend basically perpendicular to the axis. The material could also be tungsten.

Expediently, the power supply unit is located within the volume, wherein the barrier element and the power supply unit are interconnected via a power connection, in particular a flexible power connection. The flexible power connection can be a cable or something similar that is preferably more or less flexible. It goes without saying that the power connection does not have to be flexible. However, that may facilitate the handling. According to one ore more embodiments, the barrier element comprises the connector element, wherein the power connection is connected to the connector element (or elements). The same applies to a (electric) connection between the barrier element and the means for sterilization in the first chamber, in particular the electron generator. Expediently, the power connection that is located in the volume has contact or is surrounded by the first atmosphere, in particular by the insulation atmosphere. As already mentioned, the same applies to the electric interface of the barrier element or its connection element(s), respectively. As a consequence, a very sufficient insulation is provided by the first atmosphere. If gas, such as nitrogen is used, it can be made sure that every electric component within the volume is sufficiently insulated.

Advantageously, the volume comprises a radiation shield that extends basically parallel to the barrier element, wherein the radiation shield comprises or forms at least one opening, and wherein the opening extends preferably parallel to the barrier element. In particular, the radiation shield forms a labyrinth seal so that the third chamber and in particular the power supply unit or the other electric components are completely protected against radiation that is caused by the emitter or the electrons, respectively. In particular, the radiation shield provides protection against x-ray emission or gamma rays, respectively. The radiation exists when the accelerated electrons are hitting material. The electric components, as for example the power supply unit, has to be protected from the x-rays (or gamma rays etc.).

In one or more embodiments the second chamber and the third chamber are connectable at a connection area. In one or more further embodiments the radiation shield is provided in the second chamber, between the connection area and the barrier element. Furthermore, in one or more embodiments the radiation shield is provided in the third chamber, between the connection area and the power supply unit.

However, in the prior art the problem still exists that at least the area of the electric interface is a weak point with regard to radiation protection. Advantageously, according to one or more embodiments, the radiation shield comprises for example two (or more) plates that have an offset basically perpendicular to the barrier element and that overlap at least partly parallel to the barrier element. This configuration forms or generates the opening or the labyrinth seal, respectively. It goes without saying that the opening has a size and a geometry that is big enough to arrange or guide the power connection through it. As the plates overlap perpendicular to the axis, there is no way along or aligned to the axis, the x-rays or gamma-rays could pass the radiation shield. Different designs are possible to implement this idea. For example, also a plate can be provided that extends basically parallel to the barrier element, wherein the plate is as big as the cross section of the second chamber or the third chamber in this area. In other words, the plate is adapted to close the second or third chamber in this area. Advantageously, the plate comprises an opening that is adapted to guide the power connection or an electric interface through it. To "close" the opening, the radiation shield comprises a further plate that is adapted to cover the opening. Also the barrier element can form the above mentioned plate. It goes without saying that the plates are preferably made of lead or comprise lead or layers of lead, respectively. Also other materials are possible such as steel.

Expediently, the power connection is guided through the opening. Thus, it is very advantageous to use the flexible power connection as the flexible power connection can be easily guided through the opening or the labyrinth sealing, respectively. According to one or more embodiments the radiation shield, which can be located inside the second chamber as well as inside the third chamber is connected or combined with an outer radiation shield. The outer radiation shield is located outside the radiation shield and can be oriented for example perpendicular and/or along the axis. Thus the second chamber can advantageously form a space for inserting the radiation shield and/or for the flexible power connection. The materials for the outer radiation shield can be same as for the radiation shield inside the sterilization device.

In one or more embodiments an adapter element is arranged between the third chamber and the housing, wherein the adapter element can be adapted to comprise the radiation shield. The adapter element can also be arranged between the third chamber and the second chamber. According to one or more embodiments, the adapter element comprises a first and a second adapter region. The first adapter region is adapted to be connected to the connection area of the housing or the second chamber, respectively, and the second adapter region is adapted to be connected to the connection area of the third chamber. Advantageously, different sizes and/or geometries of the connection areas of the housing (or the second chamber) and the third chamber can be balanced. This allows for example the combination of different types of electron beam emitters with different power supply units or third chambers, respectively, as the size differences of the connection areas can be balanced. Expediently, the adapter element can also comprise the radiation shield which makes it possible to upgrade an existing electron beam emitter or an existing third chamber with the radiation shield technique.

According to another aspect of the invention, an electron beam emitter, in particular for sterilization of packaging material, is provided, comprising a housing and a barrier element, wherein the housing comprises at least a first chamber, wherein the first chamber is adapted to provide charge carriers for sterilization, characterized in that the housing is connectable to a third chamber so that the barrier element forms at least one part of the boundary of a volume in which a first atmosphere exists.

Advantageously, the electron beam emitter comprises an end portion. The end portion allows the arrangement of a power connection, in particular a flexible power connection and/or the arrangement of a radiation shield. The end region or top of the housing is the area that is directed to a third chamber.

According to one aspect of the invention, an adapter element, in particular for sterilization devices, comprises a first adapter region and a second adapter region, is provided. Expediently, diameters of the first and the second adapter region differ from each other. This means that cross sections of the adapter regions can be different. Expediently, the cross sections are adapted to fit to the cross sections of the connection areas of the third chamber and the housing or the second chamber, respectively, which have already been described. Advantageously, the adapter element comprises a radiation shield.

It is to be mentioned that sterilization is a term referring to any process that eliminates or kills microbial life, including transmissible agents such as for example fungi, bacteria, viruses and spores, which may be present on a surface of the packaging material or in a product. In the (food) packaging industry this is generally referred to as aseptic packaging, i. e. packaging sterilized products in sterilized packaging containers, i. e. keeping both the product and the packaging container free form living germs and microorganisms, so that the freshness of the product can be preserved without special cooling requirements, i. e. so that sterility can be maintained inside a packaging container although it is stored in ambient temperature. In this context the term "commercially sterile" is also commonly used and means in general the absence of microorganisms capable of growing in the food at normal non-refrigerated conditions at which the food is likely to be held during manufacture, distribution and storage. In this patent application the word "sterile" refers to a condition being at least commercially sterile.

The sterilization device according to the invention can include the features and advantages of the electron beam emitter according to the invention and of the adapter element according to the invention and vice versa.

Additional aspects and features of the current invention are shown in the following description of preferred embodiments of the current invention with a reference to the attached drawings. Same features or characteristics of respective embodiments are explicitly allowed to be combined within the scope of the current invention.

Figure 2A:
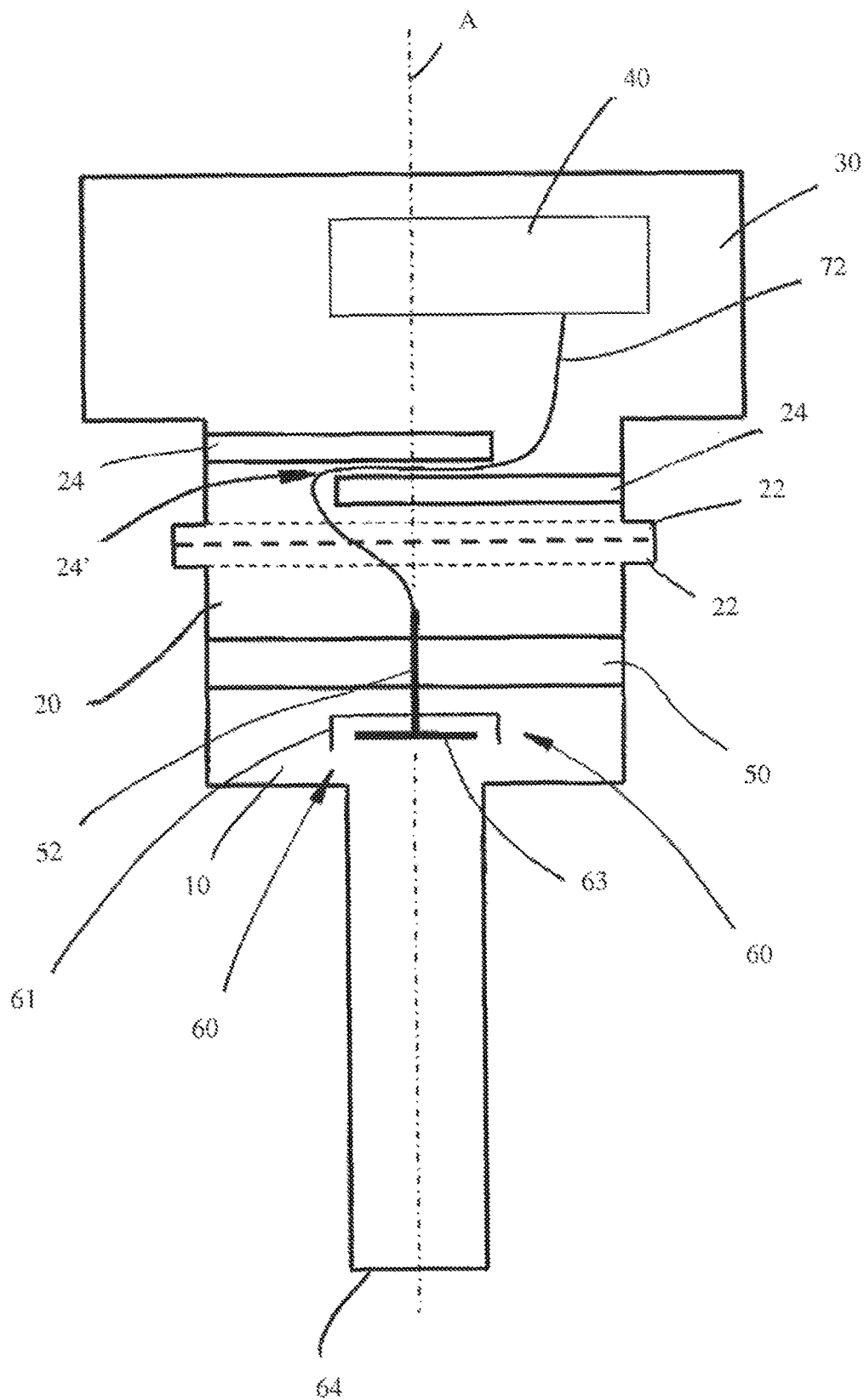
Figure 2B:
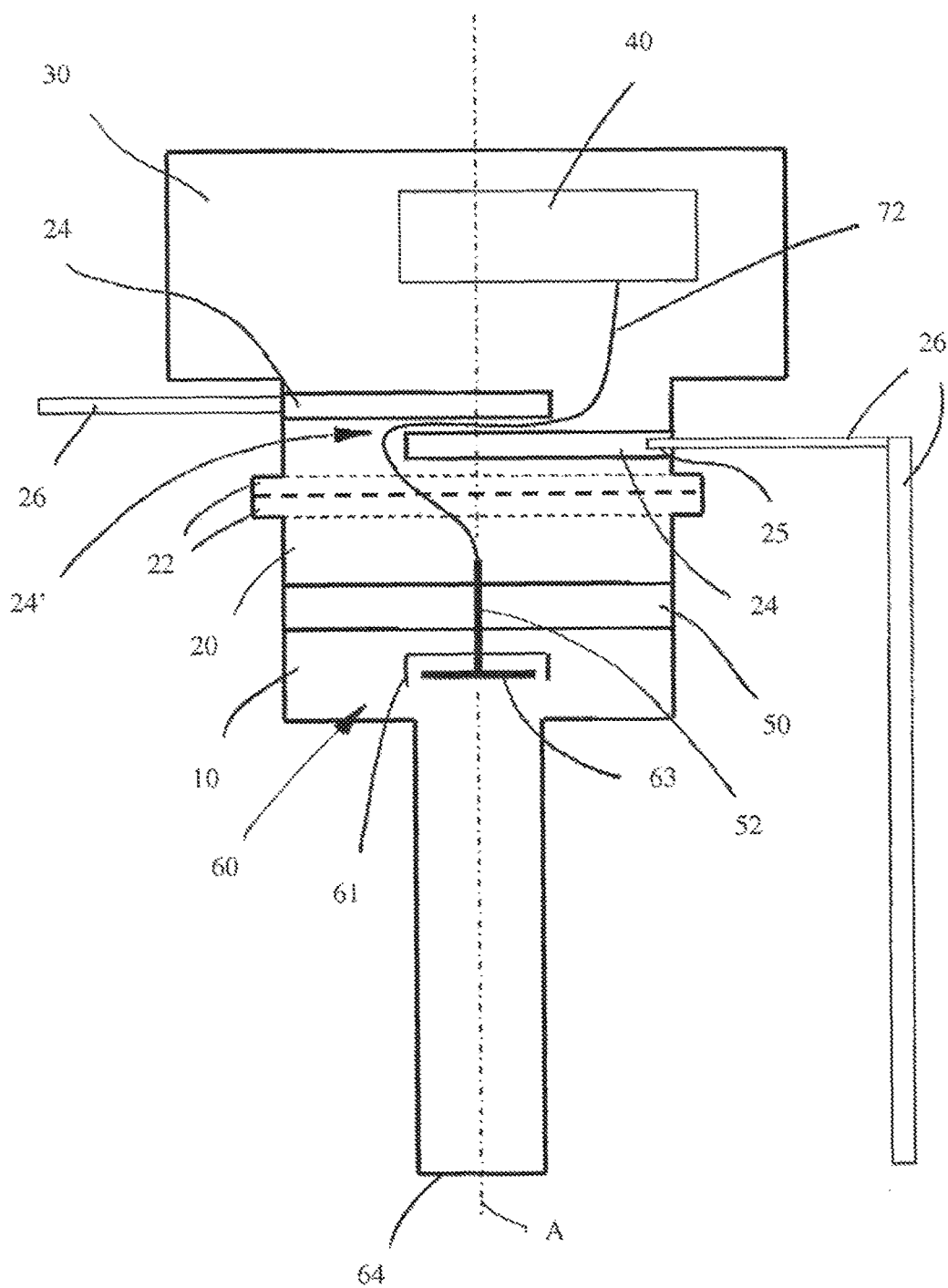
Figure 3:
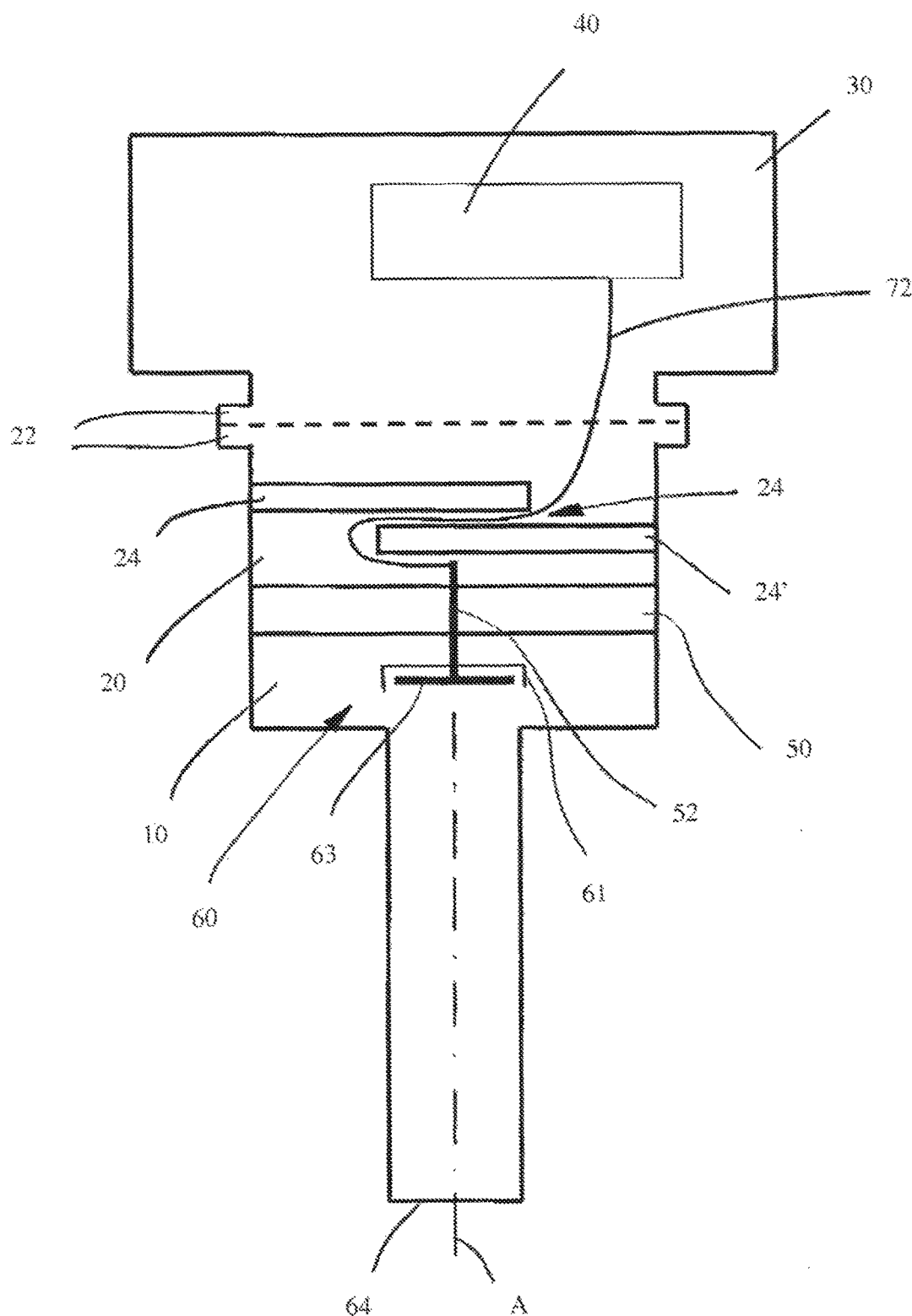
Figure 4:
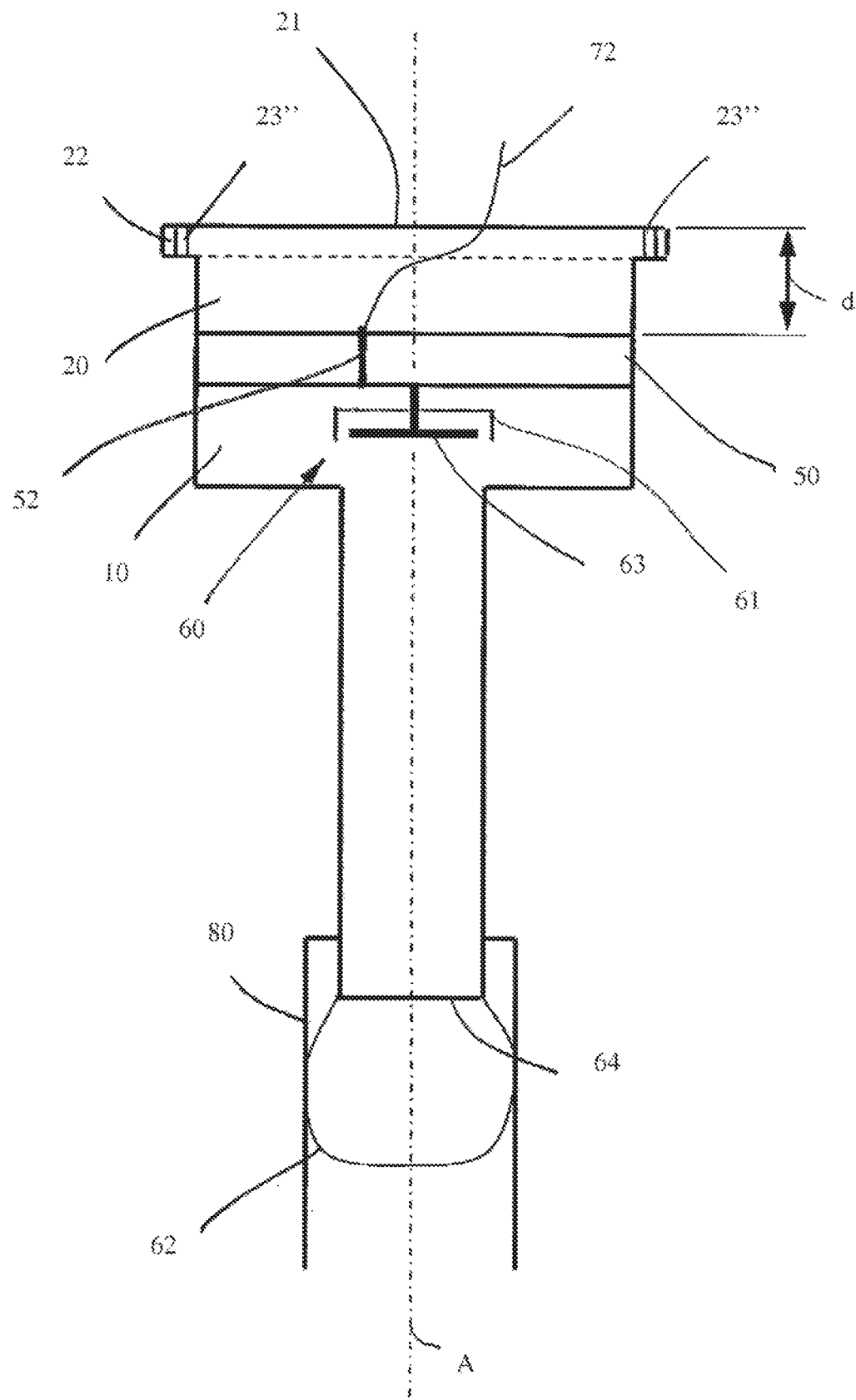
Figure 5:
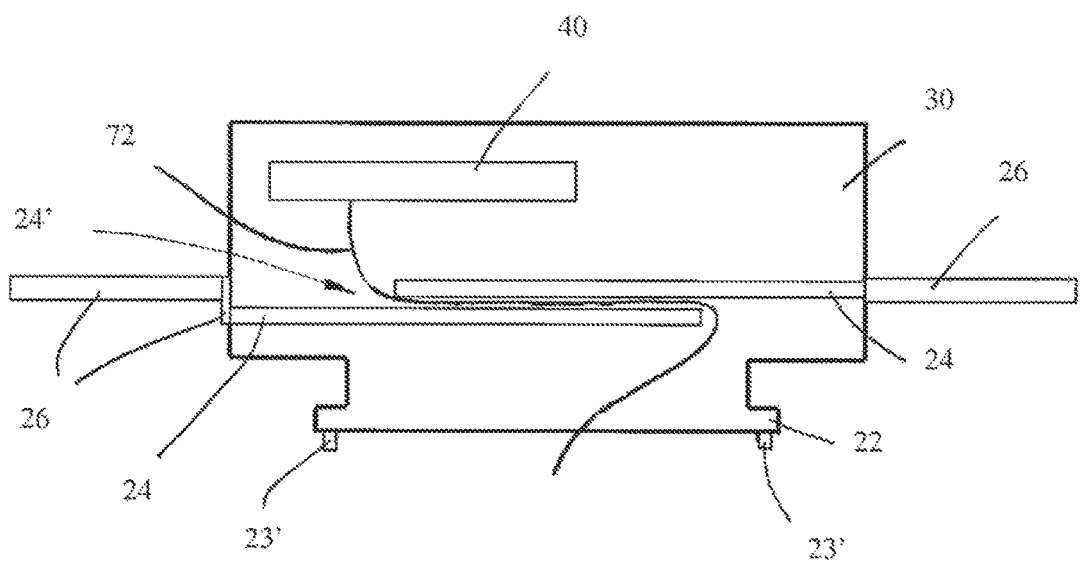
Figure 6:
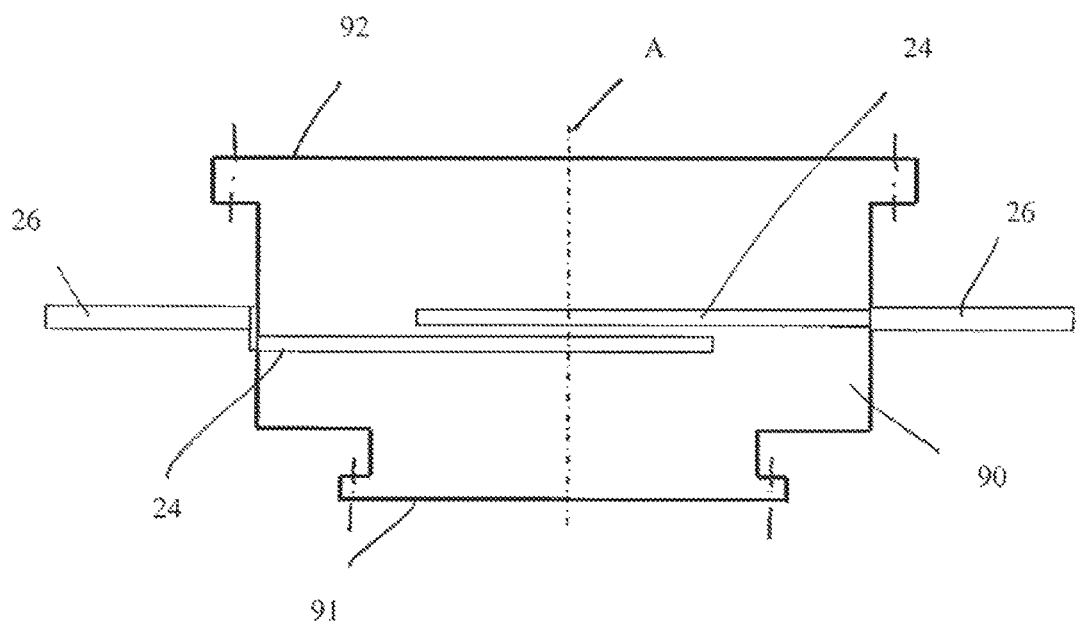
Figure 7:
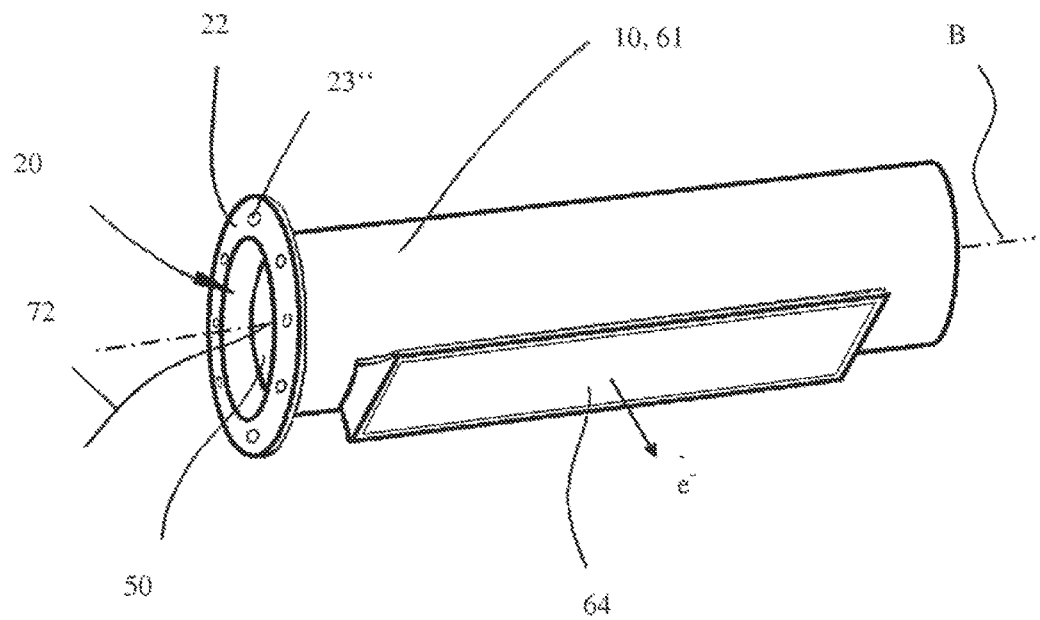
Figure 8:
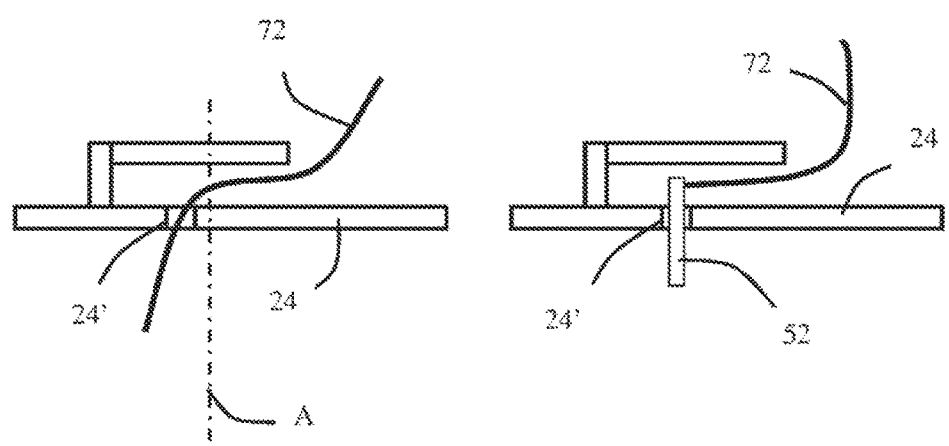
Figure 9:
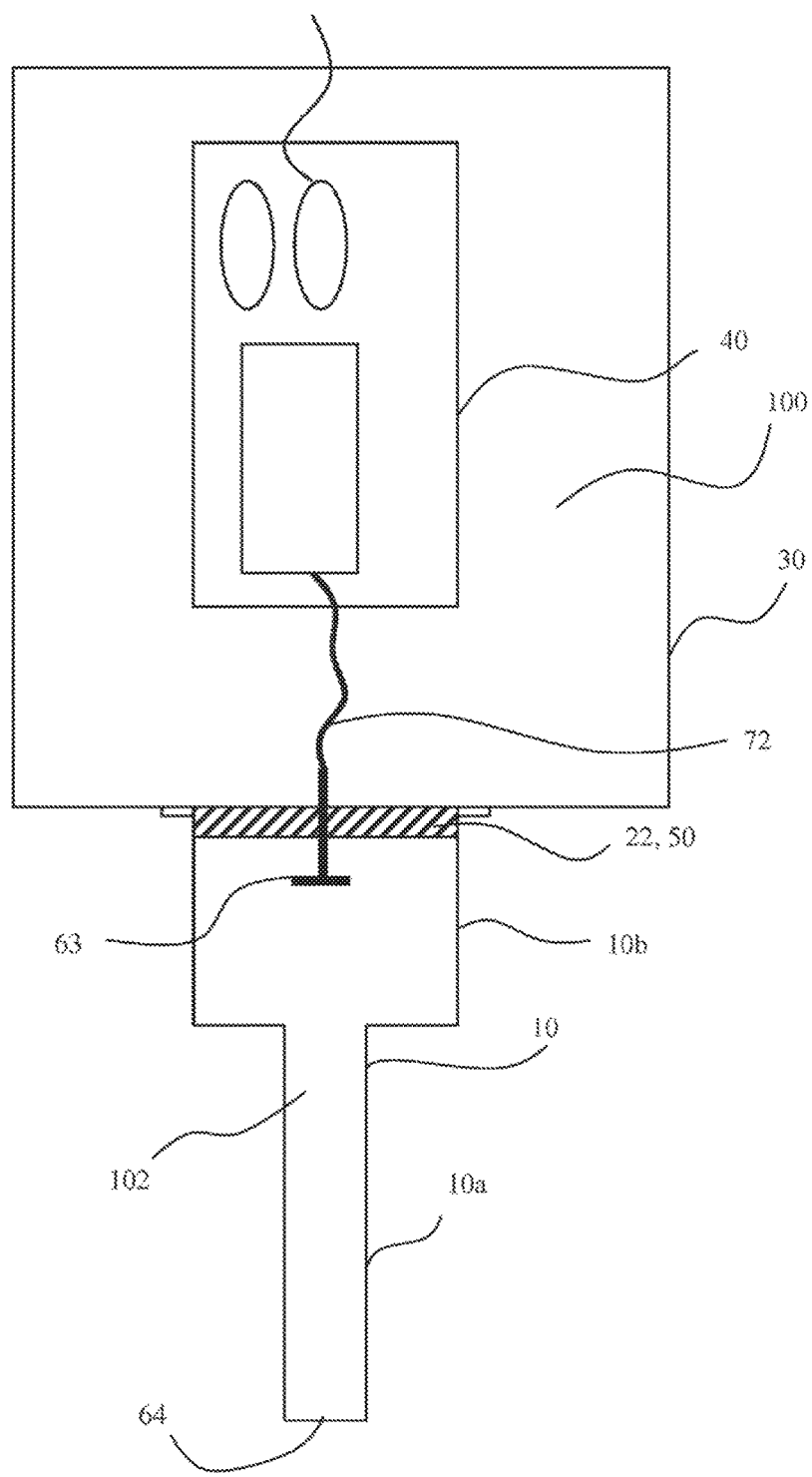
Figure 10:
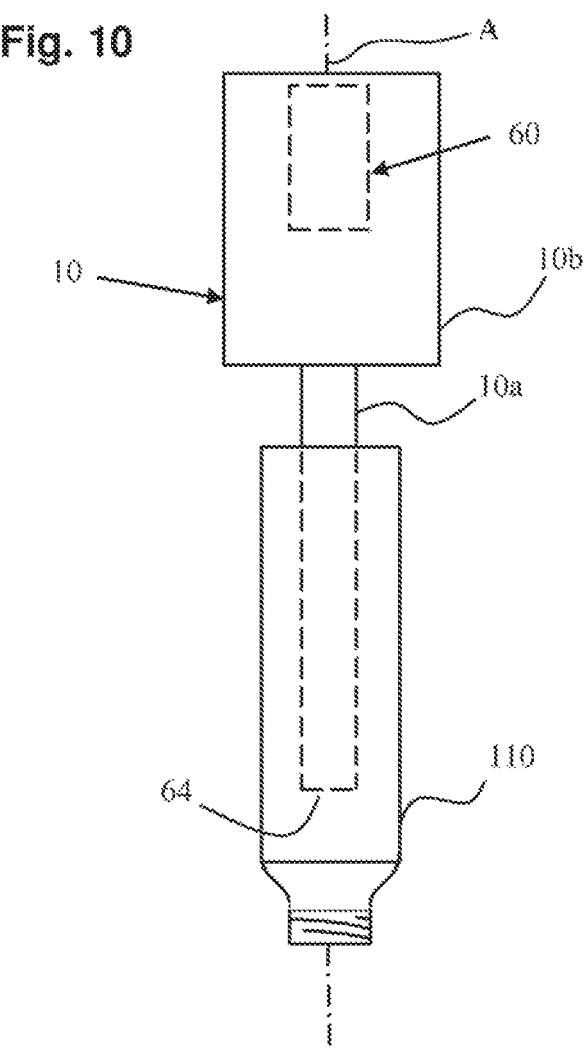

FIG. 1: shows a schematic diagram of a sterilization device according to a preferred embodiment;

FIG. 2a: shows a schematic diagram of a sterilization device according to the preferred embodiment, comprising a radiation shield that is located within the third chamber;

FIG. 2b: shows a schematic diagram of a sterilization device according to the preferred embodiment, comprising a radiation shield that is connected to an outer radiation shield FIG. 3: shows a schematic diagram of a sterilization device according to the preferred embodiment, comprising a radiation shield that is located within the second chamber FIG. 4: shows a schematic diagram of an electron beam emitter according to a preferred embodiment with a second chamber that extends along an axis;

FIG. 5: shows a schematic diagram of a third chamber according to an embodiment, comprising a radiation shield;

FIG. 6: shows an adapter element according to an embodiment, wherein the adapter element comprises a radiation shield;

FIG. 7: shows a schematic diagram of an electron beam emitter according to a further preferred embodiment;

FIG. 8: shows radiation shield according to an embodiment;

FIG. 9: shows another embodiment without a second chamber;

FIG. 10: shows a packaging container and an electron beam emitter; and

Figure 11:
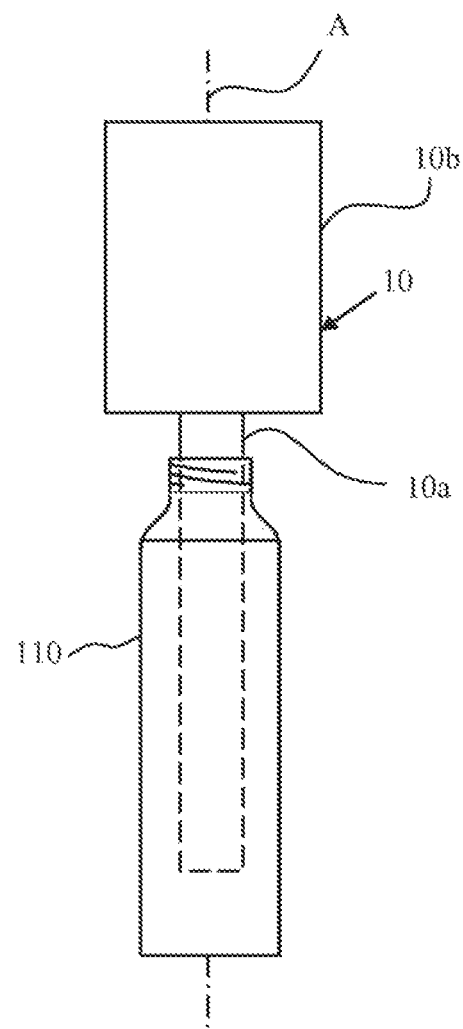

FIG. 11: shows a packaging container and an electron beam emitter.

Referring now to FIG. 1 a sterilization device is shown comprising a first chamber 10 that is separated from a second chamber 20 by a barrier element 50. The first chamber 10 comprises an electron generator 60, wherein the electron generator 60 comprises a cathode housing 61 and a filament 63. The filament 63 is adapted to emit electrons forming an electron beam. In use, the electron beam is generated by heating the filament 63. When an electrical current is fed through the filament 63, the electrical resistance of the filament 63 causes the filament 63 to be heated to a temperature in the order of 2000° C. This heating causes the filament 63 to emit electrons. The electrons are accelerated towards an electron exit window 64 by means of a high-voltage potential between the cathode housing 61 and the electron exit window 64. Subsequently, the electrons pass through the electron exit window 64 and continue towards a target area, for example a material or area, respectively, that has to be sterilized. The first chamber 10 comprises a second atmosphere 102, preferably a vacuum. A first atmosphere 100 will be described later.

According to the embodiment, the housing comprising the electron generator 60 is an electron beam emitter for sterilizing the interior of (e. g. ready-to-fill) packaging containers. The electron beam emitter comprises the electron generator 60 that is enclosed in a hermetically sealed vacuum chamber which is the first chamber 10. The vacuum chamber is provided with the electron exit window 64. Referring to FIG. 1, the first chamber 10 is preferably made up of two cylindrical bodies 10*a*, 10*b* having a common longitudinal axis A. The cylindrical bodies have circular cross section. The first cylindrical body 10*a* has an end surface, in a plane being perpendicular to the axis A, being provided with the electron exit window 64. The electron exit window 64 is preferably circular and extends over most of the end surface. The electron exit window 64 can be made of a metallic foil, such as for example titanium, and can have a thickness in the order of about 4-12 μm. A supporting structure (not shown) provided with holes supports the foil from inside the first chamber 10. The supporting structure is for example made of aluminum or copper. A diameter of the first body is small enough to be inserted e. g. into a (ready-to-fill) packaging container, the cross section of the first body is dimensioned such that it can be guided through an opening of the packaging container. Such packaging containers can be used for liquid, semi-liquid and/or solid medium. They can for example be used in the food industry or in the medical or biological area (to transport and protect biological and medical substances). However, the sterilization device may also be used for sterilization of devices, such as medical or biological devices, or food etc. The second body 10*b* is provided with the electron beam generator, and the diameter of the second body 10*b* is larger than that of the first body 10*a*. The barrier element 50 comprises an interface 52 that provides an electric connection to the electron generator 60. The second chamber 20 comprises a connection area 22 that is connected to an appropriate connection area 22 of a third chamber 30. The third chamber 30 comprises a power supply unit 40 that is connected to the interface 52 via a power connection 72.

The volume in which a first atmosphere 100 exists is formed by the third chamber 30 and the second chamber 20, wherein at least one part of a boundary of the volume is formed by the barrier element 50. Hence, the barrier element 50 forms a gas tight barrier between the first and the second atmospheres 100, 102. In this embodiment the volume, in which a first atmosphere 100 exists, is filled with gas, in particular nitrogen, wherein the gas is preferably pressurized. As a consequence, an insulation atmosphere can be provided.

FIG. 2*a* shows an embodiment that is similar to the embodiment shown in FIG. 1. However, this embodiment comprises a radiation shield 24. A second chamber 20 is separated by a barrier element 50 from a first chamber 10.

The first chamber 10 comprises an electron generator 60 that is adapted to emit charge carriers that can leave the first chamber 10 via an electron exit window 64. The electron generator 60 comprises a cathode housing 61 and a filament 63 as already known from FIG. 1. The first chamber 10 and the second chamber 20 form an electron beam emitter. The second chamber 20 comprises a connection area 22 that is formed as a flange and that is connected to a connection area 22 of a third chamber 30. Within the third chamber 30 a radiation shield 24 is arranged. The radiation shield 24 comprises two plates that have an offset along an axis A of the device, whereby an opening 24' is formed. The plates have an overlap as can be seen in the figure. The opening 24' extends basically perpendicular to the axis A. In other words, a labyrinth seal is formed. The power supply unit 40 and an interface 52 are connected via a power connection 72. Advantageously, the power connection 72 is a flexible power connection 72 that can be easily guided through the opening 24'. As a consequence, a radiation protection is provided that protects the whole chamber and in particular the power supply unit 40 from e. g. x-ray radiation generated by the electron generator 60 or its emitted electrons, respectively. In particular, radiation formed in the first chamber cannot find its way to the power supply unit 40. The radiation shield 24 is made of lead or comprises at least layers of lead, i.e. a sandwich of for example stainless steel and lead.

FIG. 2*b* shows the embodiment as already described with reference to FIG. 2*a*, however the embodiment shown in FIG. 2*b* comprises an outer radiation shield 26 that is attached or in contact, respectively, with the radiation shield 24 which is inside the third chamber 30. The radiation shield 24 which is inside the sterilization device and the outer radiation shield 26 can be just in contact as it is shown on the left side of FIG. 2*b*. Expediently, the radiation shield 24 can also comprise a recess 25 or something similar that is adapted to receive the outer radiation shield 26. It goes without saying that the outer radiation shield 26 can have different designs. This means that it can for example extend basically perpendicular to the axis A or along the axis A. It goes without saying that the outer radiation shield 26 can also be angularly declined referring to the axis A. The outer radiation shield 26 is e. g. made of lead or comprises at least layers of lead similar to the radiation shield 24 inside the sterilization device.

The radiation shield 24 is, as shown in FIG. 2*b*, positioned in the third chamber 30. The shield 24 is thus provided above the connection area 22, which area 22 is in turn positioned above the barrier element 50.

FIG. 3 shows an embodiment that is similar to the one shown in FIG. 2*a*, however, a radiation shield 24 is located inside a second chamber 20. The radiation shield 24 is positioned in between the connection area 22 and the barrier element 50.

FIG. 4 shows a schematic diagram of an electron beam emitter comprising a second chamber 20 and a first chamber 10 that are separated by a barrier element 50. This embodiment correlates to the one described in FIG. 1, however, in FIG. 4 the third chamber is not shown. The first chamber 10 comprises an electron generator 60 that is adapted to emit electrons forming an electron cloud 62, respectively. The electron cloud 62 is adapted to sterilize a packaging material 80. A diameter of the first chamber 10 is small enough to be inserted e. g. into a (ready-to-fill) packaging container 80. The cross section of the first chamber 10 is dimensioned such that it can be guided through an opening of the packaging container 10. The barrier element 50 comprises an interface 52 that is adapted to provide an electric contact with the electron generator 60. The second chamber 20 comprises a connection area 22 that is formed as a flange and that comprises a plurality of second connection elements or holes 23", respectively. The interface 52 is connected to a power connection 72 that is adapted to be connected for example to a power supply unit (not shown in this Figure). A distance d is formed between an end portion 21 of the housing, in particular of the second chamber 20, and the barrier element 50. In other words, the distance d forms the second chamber 20. The second chamber is arranged to form some space for the power connection 72.

FIG. 5 shows a schematic diagram of a third chamber 30 that comprises a connection area 22. A plurality of connection elements 23' is integrated within the connection area 22. The third chamber 30 comprises a radiation shield 24 that comprises or forms, respectively, an opening 24'. A power connection 72 is guided through the opening 24'. The power connection 27 is connected to a power supply unit 40. An outer radiation shield 26 is attached to the radiation shield 24 that is inside the third chamber 30.

FIG. 6 shows a preferred embodiment of an adapter element 90. The adapter element 90 comprises first 91 and second adapter regions 92 that comprise preferably first and second connection elements like bolts, screws, holes etc. (not shown). The embodiment shown in FIG. 6 further comprises a radiation shield 24 as it is already known form the previous figures. The radiation shield 24 is connected to an outer radiation shield 26. The adapter regions 91, 92 are orientated basically perpendicular to an axis A, wherein the axis A correlates to an electron beam direction of an electron beam emitter (not shown). The two adapter regions 91, 92 are preferably basically parallel to each other. Alternatively, also an angle could be provided.

FIG. 7 shows another embodiment of an electron beam emitter, wherein this embodiment is preferably adapted for exterior sterilization of packaging containers. Such electron beam emitter may also be used for web sterilization, for sterilization of medical or biological devices or for food etc. Such an electron beam emitter comprises a first chamber 10 that is formed as a tubular body, which has an elongate shape extending along an axis B. An electron exit window 64 provides an outlet for electrons e⁻ (of which only one is shown for illustrative purposes) from a vacuum chamber that is inside the tubular body or that is formed by the first chamber 10, respectively. The electron exit window 64 is substantially rectangular having its longest extension along axis B. The electron exit window 64 is substantially flat and protrudes from the perimeter surface of the tubular body. The electron exit window 64 can be made of a metallic foil, such as for example titanium, and can have a thickness in the order of about 4-12 µm. A supporting structure provided with holes supports the foil from inside the vacuum chamber. The supporting structure is for example made of aluminum or copper. The first chamber 10 is limited by a barrier element 50. The barrier element 50 and a connection area 22 have an offset along a longitudinal axis of the tubular body so that a second chamber 20 is formed. A power connection 72 is provided. The connection area 22 comprises a plurality of second connection elements 23".

FIG. 8 shows a radiation shield 24 according to one or more embodiments. No other components are shown. However, for orientation purposes an axis A is displayed which indicates a direction of an electron beam. The radiation shield 24 comprises a plate 24 that extends basically perpendicular to the axis A, wherein the plate is as big as a housing, a second chamber or a third chamber in this area. In other words, the plate is adapted to close the housing, the second or third chamber in this area along the axis A. It comprises an opening 24' that is adapted to guide a power connection 72 (left figure) or an electric interface 52 (right figure) through it. To "close" the opening 24', the radiation shield 24 comprises a further plate that is adapted to cover the opening 24' along the axis A. The plate that extends basically perpendicular to the axis A can also be a barrier element.

It should here be pointed out that the opening 24' cannot be as small as the diameter of the power connection 72, since the power connection 72 needs to be insulated by the first atmosphere, i.e. a certain amount of gas is needed around the power connection 72 in order to function as insulator. Alternatively, a fully insulated high voltage cable needs to be used, but generally such cables are not flexible enough, i.e. cannot be bent enough to work in the described embodiments.

FIG. 9 shows another embodiment in which the first chamber 10 of the electron beam emitter is arranged directly on the third chamber 30. The connection area 22 and the barrier element 50 are the same in this embodiment. Also the radiation shielding may be provided here. As in the other embodiments an interface 52 is arranged through the combined barrier element 50 and connection area 22, said interface 52 being connected to the filament 63 in the second atmosphere 102 and to the power connection 72 in the first atmosphere 100. The power connection 72 is connected to the power supply unit 40 provided in the third chamber. To that end, the power connection 72 is totally insulated by the gas of the first atmosphere 100, said gas being nitrogen. As in the other embodiments the first chamber comprises two bodies. A first body 10a provided with the electron exit window 64. A second body 10b provided with the electron beam generator, of which the filament 63 is a part. The second body is to be inserted into packaging containers for sterilization of the interior surface of the packaging container.

FIG. 10 shows a packaging container and an electron beam emitter of the kind being described in relation to for instance FIG. 1. The packaging container is sterilized on its inside surface by a relative movement along axis A such that a portion of the electron beam emitter is inserted into an opening of the packaging container. The first body 10a of the electron beam emitter, being provided with the electron exit window 64, is the portion being inserted into the packaging container. The packaging container is a "carton bottle" comprising a sleeve of paper-based laminated packaging material. The sleeve is closed in the end opposite the opening by a top made of thermoplastic material that is injection moulded directly on the sleeve end portion. The opening 12 of the packaging container 10 is an open bottom end, which after filling will be sealed and folded to form a substantially flat bottom surface.

FIG. 11 also shows a packaging container and an electron beam emitter. In the embodiments described in relation to FIG. 10 there is shown a large open bottom end in which the emitter is inserted. However, in this embodiment the opening is arranged in the top portion of the packaging container, as a neck or spout portion of the packaging container. The neck or spout portion will, after filling, be sealed by for instance a screw cap.

The sterilization device according to the invention can be arranged in an irradiation chamber in a filling machine. The filling machine comprises at least one filling station for filling content into the packaging container and at least one station for sealing the opening after filling. The invention can for example be applied in the application described in the international application No. PCT/EP2013/076870 filed by the applicant. A plurality of devices according to any of the embodiments described in FIGS. 1-3 herein can be provided on a carousel or the like which is adapted to rotate. The devices may be arranged in holes in the carousel and attached to the carousel in for example the connection area 22. The packaging containers, which are transported for example via a conveyor, reach the carousel and are engaged with one of the (rotating) emitters for interior surface sterilization. During at least a part of one rotation of the carousel, the interior sterilization takes place and then the packaging container is removed from the emitter or from the carousel, respectively. The packaging container is then subsequently transported through an electron cloud provided in a gap between two emitters for outside surface sterilization. The two emitters may be of the type described in relation to FIG. 7 herein.

REFERENCE NUMERALS 10 first chamber, housing
20 second chamber, housing
21 end portion
22 connection area, flange
23' first connection element, bolt/screw
23" second connection element, hole
24 radiation shield
24' opening
25 recess
26 external radiation shield
26 opening
30 third chamber
40 power supply unit
50 barrier element
52 interface
60 electron generator
61 cathode housing
62 charge carriers, electron cloud
63 filament
64 electron exit window
72 (flexible) power connection
80 packaging material, packaging container
90 adapter element
91 first adapter region
92 second adapter region
100 first atmosphere
102 second atmosphere
100 packaging container
A axis
d distance
B axis

The invention claimed is:

1. Sterilization device for sterilization of packaging material, comprising:
   a housing and a barrier element,
   a radiation shield within the housing and spaced apart from the barrier element,
   the housing comprising at least a first chamber,
   the first chamber being configured to provide charge carriers for sterilization,
   an electron generator being disposed in the first chamber, the electron generator comprising a cathode housing,
   the housing being connected to a second chamber so that the barrier element forms at least one part of a boundary of a volume in which a first atmosphere exists,
   the cathode housing being separated from the second chamber by the barrier element,
   the barrier element comprising at least one electric interface which passes through the cathode housing.

2. Sterilization device according to claim 1, wherein the volume is formed by the second chamber.

3. Sterilization device according to claim 1, wherein the electron generator further comprises a filament.

4. Sterilization device according to claim 1, wherein the volume comprises an insulation medium, and wherein the insulation medium is an insulating fluid or gas.

5. Sterilization device according to claim 1, wherein a power supply unit is located within the volume.

6. Sterilization device according to claim 5, wherein the volume comprises the radiation shield, and wherein the power supply unit is located on one side of the radiation shield and the barrier element is arranged on an opposite side of the radiation shield.

7. Sterilization device according to claim 5, wherein the electron generator and the power supply unit are connected via a power connection.

8. Sterilization device for sterilization of packaging material, comprising:
   a housing and a barrier element,
   the housing comprising at least a first chamber,
   the first chamber being configured to provide charge carriers for sterilization,
   the housing being connected to a second chamber so that the barrier element forms at least one part of a boundary of a volume in which a first atmosphere exists,
   wherein the volume is formed by the second chamber and a third chamber, said second and third chambers being connectable at a connection area.

9. Sterilization device according to claim 8, wherein a radiation shield is provided in the third chamber, between the connection area and the barrier element.

10. Sterilization device according to claim 8, wherein a radiation shield is provided in the second chamber, between the connection area and the power supply unit.

11. Sterilization device according to claim 1,
    wherein the volume comprises the radiation shield,
    wherein the radiation shield extends parallel to the barrier element and comprises or forms at least one opening, and
    wherein the opening extends parallel to the barrier element.

12. Sterilization device according to claim 11, wherein a power connection is guided through the opening.

13. Sterilization device according to claim 1, wherein an adapter element is arranged between the second chamber and the housing, and wherein the adapter element comprises a radiation shield.

14. Sterilization device according to claim 1, wherein the barrier element forms a gas tight barrier between the volume and a second atmosphere in the first chamber.

15. Sterilization device according to claim 1, wherein the volume comprises an insulation medium, the insulation medium being nitrogen.

16. Sterilization device according to claim 5, wherein the electron generator and the power supply unit are connected via a flexible power connection.

* * * * *